(12) United States Patent
Schroeder

(10) Patent No.: US 9,480,217 B2
(45) Date of Patent: Nov. 1, 2016

(54) TOMATO VARIETY NUN 00213 TOP

(71) Applicant: Nunhems B.V., AC Nunhem (NL)

(72) Inventor: Steven Schroeder, Lockeford, CA (US)

(73) Assignee: Nunhems B.V., AC Nunhem (NL)

( * ) Notice: Subject to any disclaimer, the term of this patent is extended or adjusted under 35 U.S.C. 154(b) by 0 days.

(21) Appl. No.: 14/462,665

(22) Filed: Aug. 19, 2014

(65) Prior Publication Data

US 2014/0356516 A1    Dec. 4, 2014

(51) Int. Cl.
*A01H 5/08* (2006.01)
*A01H 1/00* (2006.01)
*C12N 15/00* (2006.01)

(52) U.S. Cl.
CPC ...................... *A01H 5/08* (2013.01)

(58) Field of Classification Search
None
See application file for complete search history.

(56) References Cited

U.S. PATENT DOCUMENTS

2012/0210455 A1*  8/2012  Fowler ............... A01H 5/08
                                                            800/260

OTHER PUBLICATIONS

Larkin et al., Theor. Appl. Genet., vol. 60, 1981, pp. 197-214.*

* cited by examiner

*Primary Examiner* — Phuong Bui

(57) ABSTRACT

The invention provides a new and distinct hybrid variety of tomato, NUN 00213 TOP which is especially useful as processing tomato.

20 Claims, No Drawings

TOMATO VARIETY NUN 00213 TOP

FIELD OF THE INVENTION

The present invention relates to the field of plant breeding and, more specifically, to the development of tomato variety NUN 00213 TOP (also designated as NUN00213 TOP, NUN00213TOP, NUN00213 or NUN 00213).

BACKGROUND OF THE INVENTION

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for a uniform type over many generations become homozygous at almost all gene loci and produce a uniform population of true breeding progeny of homozygous plants. A cross between two such homozygous plants of different varieties produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

Tomato cultivars may be grouped by maturity, i.e. the time required from planting the seed to the stage where fruit harvest can occur. Standard maturity classifications include 'early', 'midseason' or late-maturing'. Another classification for tomatoes is the developmental timing of fruit set. 'Determinate' plants grow foliage, then transition into a reproductive phase of flower setting, pollination and fruit development. Consequently, determinate cultivars have a large proportion of the fruit ripen within a short time frame. Growers that harvest only once in a season favor determinate type cultivars. In contrast, 'indeterminate' types grow foliage, then enter a long phase where flower and fruit development proceed along with new foliar growth. Growers that harvest the same plants multiple times favor indeterminate type cultivars. In response to more recent consumer demands for dietary diversity, tomato breeders have developed a wider range of colors. In addition to expanding the range of red colored fruits, there are cultivars that produce fruits that are creamy white, lime green, yellow, green, golden, orange and purple. Additionally, there are multi-colored varieties exemplified by mainly red fruited varieties with green shoulders, and both striped- and variegated-colored fruit.

The fruits of tomato plants which are more suitable for processing are generally red colored and have pink to red/crimson fruit flesh.

SUMMARY OF THE INVENTION

In one aspect, the present invention provides a tomato plant of the variety designated NUN 00213 TOP. Also provided are tomato plants having all or essentially all the physiological and morphological characteristics of such plants. Parts of the tomato plant of the present invention are also provided, for example, including a leaf, pollen, an ovule, a fruit, a scion, a cutting a rootstock and a cell of the plant.

The invention also concerns seed of tomato variety NUN 00213 TOP. The tomato seed of the invention may be provided as an essentially homogeneous population of tomato seed. Therefore, seed of the invention may be defined as forming at least about 97% of the total seed, including at least about 98%, 99% or more of the seed. The population of tomato seed may be particularly defined as being essentially free from other seed. The seed population may be separately grown to provide an essentially homogeneous population of tomato plants according to the invention. Also encompassed are plants grown from seeds of tomato variety NUN 00213 TOP and plant parts thereof.

Another aspect refers to a tomato plant, or a part thereof, having all or essentially all the physiological and morphological characteristics of a tomato plant of tomato variety NUN 00213 TOP.

In still another aspect the invention relates to a plant comprising a rootstock or scion of NUN 00213 TOP.

In another aspect of the invention, a tissue culture of regenerable cells of a plant of variety NUN 00213 TOP is provided. The tissue culture will preferably be capable of regenerating plants capable of expressing all of the physiological and morphological characteristics of a plant of the invention, and of regenerating plants having substantially the same genotype as other such plants. Examples of some such physiological and morphological characteristics include those traits set forth in Table 1 herein. The regenerable cells in such tissue cultures may be derived, for example, from embryos, meristems, cotyledons, pollen, leaves, anthers, roots, root tips, pistil, flower, seed and stalk. Thus, a tissue culture may comprise regenerable cells from embryos, meristems, cotyledons, pollen, leaves, anthers, roots, root tips, pistil, flower, seed and stalk. Still further, the present invention provides tomato plants regenerated from a tissue culture of the invention, the plants having all the physiological and morphological characteristics of a plant of the invention.

In yet another aspect of the invention, processes are provided for producing tomato seeds, plants and fruit, which processes generally comprise crossing a first parent tomato plant with a second parent tomato plant, wherein at least one of the first or second parent tomato plants is a plant of the variety designated.

These processes may be further exemplified as processes for preparing hybrid tomato seed or plants, wherein a first tomato plant is crossed with a second tomato plant of a different, distinct variety to provide a hybrid that has, as one of its parents, the tomato plant variety NUN 00213 TOP.

Also provided are one or more progeny plants (offspring or descendants) of a tomato plant designated NUN 00213 TOP obtained by further breeding said variety designated NUN 00213 TOP. Said progeny plant(s) has/have essentially all physiological and morphological characteristics of variety NUN 00213 TOP when grown under the same environmental conditions. In one embodiment, said progeny plant(s) has/have (see USDA criteria): an average weight of mature fruit that is at least 83 g or preferably at least 90, 95, 100, 103 or even up to 105.1 g; an average mature fruit length (measured along the stem axis) that is at least 62 mm, or preferably 67, 71, 76, 80, 82 mm or more preferably 84.1 mm; a mature fruit diameter at the widest point of no more than 49.6 mm, or preferably 49, 48, 47.5 or more preferably 47.2 mm; an average pericarp thickness that is at least 6.7 mm, or preferably 6.9, 7.1, 7.3, 7.5 or even more preferably 7.7 mm thick; an average number of flowers in an inflorescence that is at least 5.3, or preferably 6.0, 6.6, 7.0, 7.3 or more preferably 7.5; between 1 and 4 nodes before the first inflorescence; an average number of nodes between early ($1^{st}$-$2^{nd}$, $2^{nd}$-$3^{rd}$) inflorescences that is below 2.6, or preferably below 2.3, 2.0, 1.8 or more preferably below 1.6; a large size of canopy of the plant at maximum vegetative development (compared to others of similar type); absence of leafy or running inflorescences; a fruit shape of type nr. 9 (as described in the USDA Exhibit C form for objective description of variety tomato); and a disease reaction to tomato spotted wilt virus that is resistant or exhibits few symptoms.

In one embodiment of the invention, the invention provides a method for producing a seed of a variety derived from NUN 00213 TOP comprising the steps of (a) crossing a tomato plant of variety NUN 00213 TOP with a second tomato plant; and (b) allowing seed of a variety NUN 00213 TOP-derived tomato plant to form. This method can further comprise steps of (c) crossing a plant grown from said variety NUN 00213 TOP-derived tomato seed with itself or a second tomato plant to yield additional variety NUN 00213 TOP-derived tomato seed; (d) growing said additional variety NUN 00213 TOP-derived tomato seed of step (c) to yield additional variety NUN 00213 TOP-derived tomato plants; and optionally (e) repeating the crossing and growing steps of (c) and (d) to generate further variety NUN 00213 TOP-derived tomato plants. For example, the second tomato plant is of an inbred tomato variety.

In another embodiment of the invention, tomato variety NUN 00213 TOP is crossed to produce hybrid seed of the variety designated NUN 00213 TOP. In any cross herein, either parent may be the male or female parent. In these processes, crossing will result in the production of seed. The seed production occurs regardless of whether the seed is collected or not.

In one embodiment of the invention, the first step in "crossing" comprises planting seeds of a first and a second parent tomato plant, often in proximity so that pollination will occur, for example, mediated by insect vectors. Alternatively, pollen can be transferred manually. Where the plant is self-pollinated, pollination may occur without the need for direct human intervention other than plant cultivation.

A second step may comprise cultivating or growing the seeds of the first and the second parent tomato plants into plants that bear flowers. A third step may comprise preventing self-pollination of the plants (of step 2), such as by emasculating the male portions of flowers, (e.g., treating or manipulating the flowers to produce an emasculated parent tomato plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step for a hybrid cross may comprise cross-pollination between the first and second parent tomato plants. In certain embodiments, pollen may be transferred manually or by the use of insect vectors. Yet another step comprises harvesting the seeds from at least one of the parent tomato plants. The harvested seed can be grown to produce a tomato plant or hybrid tomato plant.

The present invention also provides the tomato seeds and plants produced by a process that comprises crossing a first parent tomato plant with a second parent tomato plant, wherein at least one of the first or second parent tomato plants is a plant provided herein, such as from variety NUN 00213 TOP. In another embodiment of the invention, tomato seed and plants produced by the process are first filial generation (F1) hybrid tomato seed and plants produced by crossing a plant in accordance with the invention with another, distinct plant. The present invention further contemplates plant parts of such an F1 hybrid tomato plant, and methods of use thereof. Therefore, certain exemplary embodiments of the invention provide an F1 hybrid tomato plant and seed thereof.

In still yet another aspect, the present invention provides a method of producing a plant or a seed derived from variety NUN 00213 TOP, the method comprising the steps of: (a) preparing a progeny plant derived from said variety by crossing a plant of variety NUN 00213 TOP with a second plant; and (b) selfing the progeny plant or crossing it to the second plant or to a third plant to produce a seed of a progeny plant of a subsequent generation.

The method may additionally comprise: (c) growing a progeny plant of a further subsequent generation from said seed of a progeny plant of a subsequent generation and selfing the progeny plant of a subsequent generation or crossing it to the second, the third, or a further plant; and repeating the steps for 3 or more times, e.g., an additional 3-10 generations to produce a further plant derived from the aforementioned starting variety. The further plant derived from variety NUN 00213 TOP may be an inbred variety, and the aforementioned repeated crossing steps may be defined as comprising sufficient inbreeding to produce the inbred variety. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

The invention also concerns methods of vegetatively propagating a plant of the invention. In certain embodiments, the method comprises the steps of: (a) collecting tissue capable of being propagated from a plant of the invention; (b) cultivating said tissue to obtain proliferated shoots; and (c) rooting said proliferated shoots to obtain rooted plantlets. In some of these embodiments, the method further comprises growing plants from said rooted plantlets.

One aspect of the invention refers to a method of producing a tomato plant comprising crossing a tomato plant of variety NUN 00213 TOP with a second tomato plant one or more times. This method comprises in one embodiment selecting progeny from said crossing.

In another aspect of the invention, a plant of variety NUN 00213 TOP comprising an added heritable trait is provided, e.g., an Essentially Derived Variety of NUN 00213 TOP having one, two or three physiological and/or morphological characteristics which are different from those of NUN 00213 TOP and which otherwise has all the physiological and morphological characteristics of NUN 00213 TOP, wherein a representative sample of seed of variety NUN 00213 TOP has been deposited under NCIMB/ATTC Accession Number 42560. Physiological and morphological characteristics are considered substantially equivalent if $p \leq 0.05$. The heritable trait may comprise a genetic locus that is, for example, a dominant or recessive allele. In one embodiment of the invention, a plant of the invention is defined as comprising a single locus conversion. For example, one, two, three or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

For example, in certain embodiments, the invention provides methods of introducing a desired trait into a plant of the invention comprising: (a) crossing a plant of variety NUN 00213 TOP with a second tomato plant that comprises a desired trait to produce F1 progeny, (b) selecting an F1 progeny that comprises one, two, three or more desired trait(s), (c) crossing the selected F1 progeny with a plant of variety NUN 00213 TOP to produce backcross progeny, and (d) selecting backcross progeny comprising the desired trait(s) and which otherwise has all the physiological and morphological characteristics of variety NUN 00213 TOP. Optionally, steps (c) and (d) can be repeated one, two, three or more times such as three, four, five, six or seven times, in succession to produce selected fourth, fifth, sixth, seventh or eighth or higher backcross progeny that comprises the desired trait. The invention also provides tomato plants produced by these methods.

Still yet another aspect of the invention refers to the genetic complement of a tomato plant variety of the invention. The phrase "genetic complement" is used to refer to the aggregate of nucleotide sequences (optionally including their epigenetic modifications), the expression of which defines the phenotype of, in the present case, a tomato plant of, or a cell or tissue of that plant. A genetic complement thus represents the genetic makeup of a cell, tissue or plant, and a hybrid genetic complement represents the genetic make-up of a hybrid cell, tissue or plant. The invention thus provides tomato plant cells that have a genetic complement in accordance with the tomato plant cells disclosed herein, and plants, seeds and plants containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that a plant of the invention or a first generation progeny thereof could be identified by any of the many well-known techniques such as, for example, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (see, e.g., EP 534 858), and Single Nucleotide Polymorphisms (SNPs).

In still yet another aspect, the present invention provides hybrid genetic complements, as represented by tomato plant cells, tissues, plants, and seeds, formed by the combination of a haploid genetic complement of a tomato plant of the invention with a haploid genetic complement of a second tomato plant, preferably, another, distinct tomato plant. In another aspect, the present invention provides a tomato plant regenerated from a tissue culture that comprises a hybrid genetic complement of this invention.

In still yet another aspect, the invention provides a plant of a tomato variety that exhibits a combination of traits comprising principle uses including concentrated products, whole-pack canning and dicing. In yet another aspect the invention provides a plant of a tomato variety that exhibits a combination of traits comprising simple inflorescence, an average of three or four locules per fruit and an apple or medium green ("Heinz 1439 VF") fruit base color at mature-green stage.

Said tomato variety further exhibits at least one further trait selected from the group consisting of a moderately hairy pubescence on younger stems (USDA criterion), a medium relative maturity in area tested (9=California: Sacramento and Upper San Joaquin Valley), principle uses that include whole-pack canning, concentrated products and use as diced product and a very concentrated fruiting season (USDA criterion).

In another aspect, tomato fruits of NUN 00213 TOP have one or more traits selected from a similar or preferably a slightly higher pH than fruits of HZ 8504, and a titratable acidity (expressed as % citric acid) that is below 20, or preferably below 18, 16, 15 or even more preferably 14.8 and similar or preferably slightly lower soluble solids as °Brix.

In another preferred embodiment, in trials of disease and pest reaction plants of NUN 00213 TOP show resistance or only few symptoms to Tomato spotted wilt virus, Bacterial speck (*pseudomonas tomato*) *Fusarium* wilt race 1 and race 2 (*F. oxysporum* f. *lycopersici*), *Verticillium* wilt race 1 (*V. dahliae*) and Southern Root Knot Nematode (*Meloidogyne* spp.).

In certain embodiments, the combination of traits may be defined as controlled by genetic means for the expression of the combination of traits found in tomato variety NUN 00213 TOP.

In still yet another aspect, the invention provides a method of determining the genotype of a plant of the invention comprising detecting in the genome (e.g., a sample of nucleic acids) of the plant at least a first polymorphism. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium.

In certain embodiments, the present invention provides a method of producing tomatoes comprising: (a) obtaining a plant of the invention, wherein the plant has been cultivated to maturity, and (b) collecting tomatoes from the plant.

The invention also provides for a food or feed product comprising or consisting of a plant part described herein preferably a tomato fruit or part thereof and/or an extract from a plant part described herein. The food or feed product may be fresh or processed, e.g., canned, steamed, boiled, fried, blanched, pureed and/or frozen, etc.

Any embodiment discussed herein with respect to one aspect of the invention applies to other aspects of the invention as well, unless specifically noted.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DEFINITIONS

In the description and tables herein, a number of terms are used. In order to provide a clear and consistent understanding of the specification and claims, the following definitions are provided:

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more" unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. The terms mentioned above also comprise the term "contain" which is limited to specific embodiments. Thus, one embodiment of the invention, when the terms "comprise," "have" and "include" are used to describe a plant, part thereof or a process, refers to an embodiment wherein the limiting term "contain" is used.

"Tomato" refers herein to plants of the species *Solanum lycopersicum*.

"Cultivated tomato" refers to plants of *Solanum lycopersicum*, i.e. varieties, breeding lines or cultivars of the species *Solanum lycopersicum*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"USDA descriptors" are the plant variety descriptors described for tomato in the "Objective description of Variety Tomato *Solanum lycopersicum*", ST-470-55 (as published by U.S. Department of Agriculture, Agricultural Marketing Service, Science and Technology, Plant Variety Protection Office, Beltsville, Md. 20705 (available on the world wide web at ams.usda.gov/AMSv1.0/) and which can be downloaded from the world wide web at ams.usda.gov/AMSv1.0/getfile?dDocName=STELDEV3003738.

"UPOV descriptors" are the plant variety descriptors described for tomato in the "Guidelines for the Conduct of Tests for Distinctness, Uniformity and Stability, TG/44/10 (Geneva 2001), as published by UPOV (International Union for the Protection of New Varieties and Plants, available on the world wide web at upov.int) and which can be downloaded from the world wide web at upov.int/en/publications/tg-rom/tg044/tg_44_10.pdf and is herein incorporated by reference in its entirety.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS colour chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested tomato fruits), plant cells, plant protoplasts, plant cell and/or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, flowers, leaves, seeds, clonally propagated plants, roots, stems, root tips, grafts, parts of any of these and the like. Also any developmental stage is included, such as seedlings, cuttings prior or after rooting, mature plants or leaves.

"Harvested plant material" refers herein to plant parts (e.g. a fruit detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and morphological characteristics" means a plant having essentially all or all the physiological and morphological characteristics when grown under the same environmental conditions of the plant of NUN 00213 TOP from which it was derived, e.g. the progenitor plant, the parent, the recurrent parent, the plant used for tissue- or cell culture, etc. The skilled person will understand that a comparison between tomato varieties should occur when said varieties are grown under the same environmental conditions. For example, the plant may have all characteristics mentioned in Table 1. In certain embodiments, the plant having "essentially all the physiological and morphological characteristics" are plants having all the physiological and morphological characteristics, except for certain characteristics, such as one, two or three, mentioned, e.g. the characteristic(s) derived from a converted or introduced gene or trait and/or except for the characteristics which differ in an EDV.

So, the plant may have all characteristics mentioned in Table 1, except for one, two or three characteristics of Table 1, in which the plant may thus differ.

"Distinguishing characteristics" or "distinguishing morphological and/or physiological characteristics" refers herein the characteristics which are distinguishing between NUN 00213 TOP and other tomato varieties, such as Heinz 8504, when grown under the same environmental conditions, especially the following characteristics: 1) mature fruit weight; 2) mature fruit length (along stem axis); 3) mature fruit diameter (at widest point); 4) thickness of pericarp; 5) number of flowers per inflorescence; 6) number of nodes before the first inflorescences; 7) number of nodes between early inflorescences; 8) a large size of canopy; 9) absence of running inflorescences; 10) type of fruit shape and 11) resistance to tomato spotted wilt virus. In one aspect, the distinguishing characteristics further include at least one, two, three or more (or all) of the characteristics listed in Table 1.

Thus, a tomato plant "comprising the distinguishing characteristics of NUN 00213 TOP", refers herein to a tomato plant which does not differ significantly from NUN 00213 TOP in characteristics 1) to 6) above. In a further aspect the tomato plant further does not differ significantly from NUN 00213 TOP in one or more, or all characteristics 7) to 11) as mentioned above. In yet a further aspect the tomato plant further does not differ in at least one, two, three, four, five or six characteristics selected from the characteristics listed in Table 1.

The physiological and/or morphological characteristics mentioned above are commonly evaluated at significance levels of 1%, 5%, 8% or 10% significance level, when measured under the same environmental conditions. For example, a progeny plant of NUN 00213 TOP may have one or more (or all, or all except one, two or three) of the essential physiological and/or morphological characteristics of NUN 00213 TOP listed in Table 1, or one or more or all (or all except one, two or three) of the distinguishing characteristics of NUN 00213 TOP listed in Table 1 and above, as determined at the 1% or 5% significance level when grown under the same environmental conditions.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

The terms "gene converted" or "conversion plant" in this context refer to tomato plants which are often developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are often developed by plant breeding techniques comprising or consisting of backcrossing, wherein essentially all of the desired morphological and physiological characteristics of a tomato variety are recovered in addition to the characteristics of the single locus having been transferred into the variety via, e.g., the backcrossing technique and/or by genetic transformation. Likewise, a double loci converted plant/a triple loci converted plant refers to plants having essentially all of the desired morphological and physiological characteristics of given variety, expect that at two or three loci, respectively, it contains the genetic material (e.g., an allele) from a different variety.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety.

Thus, an EDV may be obtained for example by the selection of a natural or induced mutant, or of a somaclonal variant, the selection of a variant individual from plants of the initial variety, backcrossing, or transformation by genetic engineering. In one embodiment, an EDV is a gene converted plant.

"Plant line" is for example a breeding line which can be used to develop one or more varieties.

"Hybrid variety" or "F1 hybrid" refers to the seeds of the first generation progeny of the cross of two non-isogenic plants. For example, the female parent is pollinated with pollen of the male parent to produce hybrid (F1) seeds on the female parent.

"Progeny" as used herein refers to plants derived from a plant designated NUN 00213 TOP. Progeny may be derived by regeneration of cell culture or tissue culture or parts of a plant designated NUN 00213 TOP or selfing of a plant designated NUN 00213 TOP or by producing seeds of a plant designated NUN 00213 TOP. In further embodiments, progeny may also encompass plants derived from crossing of at least one plant designated NUN 00213 TOP with another tomato plant of the same or another variety or (breeding) line, or with a wild tomato plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of NUN 00213 TOP which are EDVs or which retain all (or all except 1, 2 or 3) physiological and/or morphological characteristics of NUN 00213 TOP listed in Table 1, or which retain all (or all except 1, 2, or 3) of the distinguishing characteristics of NUN 00213 TOP described elsewhere herein and in Table 1, are encompassed herein.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one tomato line or variety to another.

"Crossing" refers to the mating of two parent plants. The term encompasses "cross-pollination" and "selfing".

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, protoplasts, meristematic cell, root, root tip, pistil, anther, flower, shoot tip, shoot, stem, petiole, etc. When a whole plant is regenerated by vegetative propagation, it is also referred to as a vegetative propagation.

"Locus" (plural loci) refers to the specific location of a gene or DNA sequence on a chromosome. A locus may confer a specific trait.

"Linkage" refers to a phenomenon wherein alleles on the same chromosome tend to segregate together more often than expected by chance if their transmission was independent.

"Marker" refers to a readily detectable phenotype, preferably inherited in co-dominant fashion (both alleles at a locus in a diploid heterozygote are readily detectable), with no environmental variance component, i.e., a heritability of 1.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e. diploid, these chromosomes are referred to as homologous chromosomes. Diploid organisms have one copy of each gene (and therefore one allele) on each chromosome. If both alleles are the same, they are homozygotes. If the alleles are different, they are heterozygotes.

As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield (i.e. intermediate resistance). Some plants that are referred to as resistant or tolerant are only so in the sense that they may still produce a crop, even though the plants are stunted and the yield is reduced.

"Tissue Culture" refers to a composition comprising isolated cells of the same or a different type or a collection of such cells organized into parts of a plant.

"Transgene" or "chimeric gene" refers to a genetic locus comprising a DNA sequence which has been introduced into the genome of a tomato plant by transformation. A plant comprising a transgene stably integrated into its genome is referred to as "transgenic plant".

"Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Triploid" refers to a cell or organism having three sets of chromosomes.

"Tetraploid" refers to a cell or organism having four sets of chromosomes.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for tomato described herein. The mean, if not indicated otherwise within this application, refers to the arithmetic mean of measurements on at least 10 different, randomly selected plants of a variety or line.

"Substantially equivalent" refers to a characteristic that, when compared, does not show a statistically significant difference from the mean (e.g., $p \leq 0.05$ or less, the skilled person knows that Analysis of variance (ANOVA) is a suitable tool for determining a p value).

DETAILED DESCRIPTION OF THE INVENTION

The invention provides methods and compositions relating to plants, plant parts, seeds and progenies of tomato variety NUN 00213 TOP.

Variety NUN 00213 TOP is most similar to the commercially available variety Heinz 8504. However, NUN 00213 TOP differs from Heinz 8504 in one or more, e.g. at least two, at least three, at least four, or more, optionally all morphological and/or physiological characteristics listed in the following (see USDA criteria and also Table 1), when grown under the same environmental conditions:

i. NUN 00213 TOP has a mature fruit weight that is at least 15% higher, preferably at least 20%, 22%, 24%, 26% or even more preferably at least 26.5% higher than the mature fruit weight of Heinz 8504.

ii. NUN 00213 TOP has a mature fruit length (along stem axis) that is at least 25% higher, preferably at least 30%, 32%, 34%, 36% or even more preferably at least 37.4% higher than the mature fruit weight of Heinz 8504.

iii. NUN 00213 TOP has a mature fruit diameter (at widest point) that is at least 2% lower, preferably at least 3%, 4%, 4.5% or even more preferably at least 5% lower than the mature fruit weight of Heinz 8504.

iv. NUN 00213 TOP has a pericarp that is at least 10%, preferably at least 12%, 13%, 14% or even 14.9% thicker than the pericarp of Heinz 8504.

v. NUN 00213 TOP has a number of flowers per inflorescence that is at least 25% higher, or preferably 30%, 35%, 37.5%, 40% or even more preferably 42.1% higher than the number of flowers per inflorescence of Heinz 8504.

vi. NUN 00213 TOP has a number of nodes before first inflorescence that is at least 30% lower, or preferably 35%, 37.5%, 40%, 42.5% or even more preferably 45% lower than the number of nodes before first inflorescence of Heinz 8504.

vii. NUN 00213 TOP has a number of nodes between early ($1^{st}$-$2^{nd}$, $2^{nd}$-$3^{rd}$) inflorescences that is at least 25% lower, or preferably 30%, 32.5%, 35%, 37.5% or even more preferably 38.5% lower than the number of nodes between early ($1^{st}$-$2^{nd}$, $2^{nd}$-$3^{rd}$) inflorescences of Heinz 8504.

viii. NUN 00213 TOP has large size of canopy (compared to others of similar type) of the mature plant (at maximum vegetative development), whereas Heinz 8504 has a medium size of canopy.

ix. NUN 00213 TOP has absent running inflorescences, whereas Heinz 8504 has occasional running inflorescences.

x. NUN 00213 TOP has a typical fruit shape of nr. 9, whereas Heinz 8504 has a typical shape of nr. 10 for their typical shape in longitudinal section (see USDA Exhibit C of tomato).

xi. NUN 00213 TOP has resistance/few symptoms against bacterial speck (*Pseudomonas tomato*), *fusarium* wilt race 1 and 2 (*F. oxysporum* f. *lycopersici*) *Verticillium* wilt race 1 (*V. dahliae*) and Southern root knot nematode (*Meloidogyne* spp.), whereas Heinz 8504 is highly resistant for these 3 diseases. Also, NUN 00213 TOP has resistance/few symptoms against Tomato spotted wilt virus.

In one aspect the invention relates to an Essentially Derived Variety of NUN 00213 TOP having one, two or three physiological and/or morphological characteristics which are different from those of NUN 00213 TOP and which otherwise has all the physiological and morphological characteristics of NUN 00213 TOP, wherein a representative sample of seed of variety NUN 00213 TOP has been deposited under Accession Number NCIMB 42560.

Breeding of Tomato Plants of the Invention

One aspect of the current invention concerns methods for crossing a tomato variety provided herein with itself or a second plant and the seeds and plants produced by such methods. These methods can be used for propagation of a variety provided herein, or can be used to produce hybrid tomato seeds and the plants grown therefrom. Such hybrid seeds can be produced by crossing the parent varieties of the variety.

The development of new varieties using one or more starting varieties is well known in the art. In accordance with the invention, novel varieties may be created by crossing a plant of the invention followed by multiple generations of breeding according to such well known methods. New varieties may be created by crossing with any second plant. In selecting such a second plant to cross for the purpose of developing novel varieties, it may be desired to choose those plants that either themselves exhibit one or more selected desirable characteristics or that exhibit the desired characteristic(s) when in hybrid combination. Once initial crosses have been made, inbreeding and selection take place to produce new varieties. For development of a uniform variety, often five or more generations of selfing and selection are involved.

Uniform varieties of new varieties may also be developed by way of double-haploids. This technique allows the creation of true breeding varieties without the need for multiple generations of selfing and selection. In this manner, true breeding varieties can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous variety.

Backcrossing can also be used to improve an inbred plant. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term variety NUN 00213 TOP is used in the context of the present invention, this also includes plants modified to include at least a first desired heritable trait such as one, two or three desired heritable trait(s).

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross are then mated back to the recurrent parent followed by selection in the resultant progeny (first backcross generation, or BC1) for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental tomato plant which contributes the desired characteristic or characteristics is termed the non-recurrent parent because it can be used one time in the backcross protocol and therefore need not recur. The parental tomato plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent variety was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous or hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of tomato plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of tomato are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

Tomato varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Tomatoes are grown for use as rootstocks or scions. Typically, different types of tomatoes are grafted to enhance disease resistance, which is usually conferred by the rootstock, while retaining the horticultural qualities usually conferred by the scion. It is not uncommon for grafting to occur between *Solanum lycopersicum* varieties and related *Solanum* species. Methods of grafting and vegetative propagation are well-known in the art.

The varieties and varieties of the present invention are particularly well suited for the development of new varieties or varieties based on the elite nature of the genetic background of the variety. In selecting a second plant to cross with NUN 00213 TOP for the purpose of developing novel tomato varieties, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), male fertility, improved harvest characteristics, enhanced nutritional quality, increased antioxidant content, improved processing characteristics, high yield, improved characteristics related to the fruit flavor, texture, size, shape, durability, shelf life, and yield, improved vine habit, increased soluble solids content, uniform ripening, delayed or early ripening, reduced blossom end scar size, seedling vigor, adaptability for soil conditions, and adaptability for climate conditions. Qualities that may be desirable in a processing tomato are not necessarily those that would be desirable in a fresh market tomato; thus, the selection process for desirable traits for each specific end use may be different. For example, certain features, such as solids content, and firm fruit to facilitate mechanical harvesting are more desirable in the development of processing tomatoes; whereas, external features such as intensity and uniformity of fruit color, unblemished fruit, and uniform fruit size are typically more important to the development of a fresh market product that will have greater retailer or consumer appeal. Of course, certain traits, such as disease and pest resistance, high yield, and concentrated fruit set are of interest in any type of tomato variety or variety.

Using methods known in the art like "reverse breeding", it is possible to produce parental lines for a hybrid plant such as NUN 00213 TOP; where normally the hybrid is produced from the parental lines. Such methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 00213 TOP) comprising the step of making double haploid cells from haploid cells from the plant of the invention (NUN 00213 TOP) or a seed of that plant; and optionally crossing these parental lines to produce and collect seeds. In another aspect, the invention relates to a combination of parental lines produced by this method. In still another aspect said combination of parental lines can be used to produce a seed or plant of NUN 00213 TOP when these parental lines are crossed. In still another aspect, the invention relates to a combination of parental lines from which a seed or plant of an EDV of NUN 00213 TOP can be produced or in another aspect, wherein a seed or plant having the distinguishing characteristics 1)-6) or 1)-11) of NUN 00213 TOP, as herein defined, can be produced when grown under the same environmental conditions. In still another aspect, the invention relates to a combination of parental lines from which a seed or plant having all the characteristics of NUN 00213 TOP as defined in Table 1 can be produced when grown under the same conditions. It is understood that "can be produced" as referred to in these embodiments should be read in such a way that the plant having the specified characteristics is obtained as progeny by crossing the specified combination of parental lines.

Plants of the Invention Derived by Genetic Engineering

Many useful traits that can be introduced by backcrossing, as well as directly into a plant, are those that are introduced by genetic transformation techniques. Genetic transformation may therefore be used to insert a selected transgene into the tomato variety of the invention or may, alternatively, be used for the preparation of varieties containing transgenes that can be subsequently transferred to the variety of interest by crossing. Methods for the transformation of plants, including tomato, are well known to those of skill in the art.

Techniques which may be employed for the genetic transformation of tomato include, but are not limited to, electroporation, microprojectile bombardment, *Agrobacterium*-mediated transformation, pollen-mediated transformation, and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

To effect pollen-mediated transformation, one may apply pollen pretreated with DNA to the female reproduction parts of tomato plants for pollination. A pollen-mediated method for the transformation of tomato is disclosed in U.S. Pat. No. 6,806,399.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the BIOLISTICS Particle Delivery System, which can be used to propel particles coated with DNA or cells through a screen, such as a stainless steel or Nytex screen, onto a surface covered with target tomato cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant species where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (see, e.g., U.S. Pat. No. 5,563,055).

Transformation of plant protoplasts also can be achieved using methods based on calcium phosphate precipitation, polyethylene glycol treatment, electroporation, and combinations of these treatments which are well known in the art. Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for tomato plant gene expression include, but are not limited to, the cauliflower mosaic virus (CaMV) P-35S promoter, which confers constitutive, high-level expression in most plant tissues, including monocots; a tandemly, partially duplicated version of the CaMV 35S promoter, the enhanced 35S promoter (P-e35S) the nopaline synthase promoter, the octopine synthase promoter; and the figwort mosaic virus (P-FMV) promoter (see, e.g., U.S. Pat. No. 5,378,619) and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding; or (5) chemicals such as methyl jasmonate, salicylic acid, or Safener. It may also be advantageous to employ organ-specific promoters.

Exemplary nucleic acids which may be introduced to the tomato varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a tomato plant according to the invention. Non-limiting examples of particular genes and corresponding phenotypes one may choose to introduce into a tomato plant include one or more genes for insect tolerance, such as a *Bacillus thuringiensis*

(B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. No. 5,500,365 and U.S. Pat. No. 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. Thus, any gene which produces a protein or mRNA which expresses a phenotype or morphology change of interest is useful for the practice of the present invention.

DEPOSIT INFORMATION

A total of 2500 seeds of the hybrid variety NUN 00213 TOP were deposited according to the Budapest Treaty by Nunhems B.V. on Mar. 17, 2016, at the NCIMB Ltd., Ferguson Building, Craibstone Estate, Bucksburn, Aberdeen AB21 9YA, United Kingdom (NCIMB). The deposit has been assigned Accession Number NCIMB 42560.

A deposit of NUN 00213 TOP and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXPERIMENTS

Development of NUN 00213 TOP

The hybrid NUN 00213 TOP was developed from a male and female proprietary inbred line of Nunhems. The female and male parents were crossed to produce hybrid (F1) seeds of NUN 00213 TOP. The seeds of NUN 00213 TOP can be grown to produce hybrid plants and parts thereof (e.g. tomato fruit). The hybrid NUN 00213 TOP can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant concluded that NUN 00213 TOP is uniform and stable.

HEINZ 8504 is considered to be the most similar to NUN 00213 TOP. HEINZ 8504 is a commercial variety from Heinz Seed (H.J. Heinz Company). In Table 1 a comparison between NUN 00213 TOP and HEINZ 8504 is shown based on a trial in the USA, location: Acampo, Calif., USA (coordinates: 38.192873N, 121.232637W). Transplanting date: Apr. 17, 2013.

Two replications of 50 plants each, from which 15 plants or plant parts were randomly selected, were used to measure characteristics. In Table 1 the USDA descriptors of NUN 00213 TOP (this application) and reference HEINZ 8504 (commercial variety) are listed.

In accordance with one aspect of the present invention, there is provided a plant having the physiological and morphological characteristics of tomato variety NUN 00213 TOP. A description of the physiological and morphological characteristics of tomato variety NUN 00213 TOP is presented in Table 1.

TABLE 1

Comparison between NUN 00213 TOP and HEINZ 8504

|  | NUN 00213 TOP | HEINZ 8504 |
|---|---|---|
| Observation trial planted in: | Field | Field |
| Observation trial planting type: | Transplant | Transplant |
| Dates of seeding/transplanting | Apr. 17, 2013 (Acampo, CA, USA) | Apr. 17, 2013 (Acampo, CA, USA) |
| Observation trial planting type: | Transplanted and unstaked | Transplanted and unstaked |
| Seedling: | | |
| Anthocyanin in hypocotyl of 2-15 cm 1 = absent; 2 = present | 2 | / |
| Habit of 3-4 week old seedling 1 = normal; 2 = compact | 1 | 1 |
| Mature plant: | | |
| Height | 51.1 cm | 51 cm |
| Growth type 1 = indeterminate; 2 = determinate | 2 | 2 |
| Form 1 = lax; 2 = normal; 3 = compact; 4 = dwarf; 5 = brachytic | 3 | 3 |
| Size of canopy (compared to similar form) 1 = small; 2 = medium; 3 = large | 3 | 2 |
| Habit 1 = sprawling; 2 = semi-erect; 3 = erect (Dwarf Champion) | 2 | 2 |
| Stem | | |
| Branching 1 = sparse (Brehm's Solid Red; Fireball); 2 = intermediate (Westover); 3 = profuse (UC 82) | 3 | 3 |
| Branching at cotyledon or first leafy node 1 = present; 2 = absent | 2 | 2 |
| Number of nodes before first inflorescence | 1-4 | 7-10 |
| Number of nodes between early ($1^{st}$ to $2^{nd}$, $2^{nd}$ to $3^{rd}$) inflorescence | 1.6 | 2.6 |

TABLE 1-continued

Comparison between NUN 00213 TOP and HEINZ 8504

| | NUN 00213 TOP | HEINZ 8504 |
|---|---|---|
| Number of nodes between later developing inflorescences | 1 | not determined |
| Pubescence on younger stems<br>1 = smooth (no long hairs); 2 = sparsely hairy (scattered long hairs); 3 = moderately hairy; 4 = densely hairy or wooly | 2 | 3 |
| Leaf: | | |
| Type:<br>1 = tomato; 2 = potato (Trip-L-Crop) | 1 | 1 |
| Morphology (corresponding to Exhibit C illustration) | 2 | 2 |
| Margins of major leaflets<br>1 = absent; 2 = shallowly toothed or scalloped; 3 = deeply toothed or cut, sps. towards base | 2 | 2 |
| Marginal rolling or wiltness<br>1 = absent; 2 = slight; 3 = moderate; 4 = strong | 3 | 3 |
| Onset of leaflet rolling<br>1 = early-season; 2 = mid-season; 3 = late-season | 2 | 2 |
| Surface of major leaflets<br>1 = smooth; 2 = rogues (bumpy or veiny) | 2 | 2 |
| Pubescence<br>1 = smooth (no long hairs); 2 = normal; 3 = hirsute; 4 = wooly | 2 | 2 |
| Inflorescence: | | |
| Type<br>1 = simple; 2 = forked (2 major axes); 3 = compound (much branched) | 1 | 1 + 2 |
| Number of flowers in inflorescence average | 7.5 | 5.27 |
| Leafy or "running" inflorescence<br>1 = absent; 2 = occasional; 3 = frequent | 1 | 2 |
| Flower: | | |
| Calyx<br>1 = normal, lobes awl-shaped; 2 = macrocalyx, lobes large, leaflike; 3 = fleshy | 1 | 1 |
| Calyx-lobes<br>1 = shorter the corolla; 2 = approx., equaling corolla; 3 = distinctly longer than corolla | 1 | 1 |
| Corolla color<br>1 = yellow: 2 = old gold; 3 = white or tan | 1 | 1 |
| Style pubescence<br>1 = absent; 2 = sparse; 3 = dense | 1 | 1 |
| Anthers<br>1 = all fused into tube; 2 = separating into 2 or more groups at anthesis | 1 | 1 |
| Fasciation (1st flower of 2$^{nd}$ or 3$^{rd}$ inflorescence)<br>1 = absent; 2 = occasionally present; 3 = frequently present | 1 | 1 |
| Fruit: | | |
| Typical shape (corresponding to Exhibit C illustration) | 9 | 10 |
| Shape of transverse section<br>1 = round; 2 = flattened; 3 = angular; 4 = irregular | 1 | 1 |
| Shape of stem end<br>1 = flat; 2 = indented | 1 | 2 |
| Shape of blossom end<br>1 = indented; 2 = flat; 3 = nippled; 4 = tapered | 4 | 2 |
| Shape of pistil scar<br>1 = dot; 2 = stellate; 3 = linear; 4 = irregular | 1 | 1 |
| Abscission layer<br>1 = present (pedicellate); 2 = absent (jointless) | 2 | 2 |
| Point of detachment of fruit at harvest<br>1 = at pedicel joint; 2 = at calyx attachment | 2 | 2 |
| Length of pedicel (from joint to calyx attachment) | Not applicable | Not applicable |
| Length of mature fruit (stem axis) | 84.1 mm | 61.8 mm |
| Diameter of fruit at widest point | 47.2 mm | 49.6 mm |
| Weight of mature fruit | 105.1 g | 83.1 g |
| Number of locules<br>1 = two; 2 = three or four; 3 = five or more | 2 | 1/2 |
| Fruit surface<br>1 = smooth; 2 = slightly rough; 3 = moderately rough or ribbed | 1 | 1 |
| Fruit base color (mature-green stage)<br>1 = light green (Lanal; VF 145-F5); 2 = light gray-green; 3 = apple or medium green (Heinz 1439 VF); 4 = yellow green; 5 = dark green | 3 (e.g. RHS Yellow Green 144D) | 1 |
| Fruit pattern (mature-green stage)<br>1 = uniform green; 2 = green-shouldered; 3 = radial stripes on sides of fruit | 1 | 1 |
| Shoulder color if different from base<br>1 = dark green; 2 = grey green; 3 = yellow green | Not applicable | Not applicable |
| Fruit color full ripe:<br>1 = white; 2 = yellow; 3 = orange; 4 = pink; 5 = red; 6 = brownish 7 = greenish; 8 = other | 5 | 5 |
| Flesh color full ripe:<br>1 = yellow; 2 = pink; 3 = red/crimson; 4 = orange; 5 other | 3 | 3 |
| Flesh color:<br>1 = uniform; 2 = with lighter and darker areas in walls | 1 | 1 |
| Locular gel color of table-ripe fruit<br>1 = green; 2 = yellow; 3 = red | 3 | 3 |
| Ripening<br>1 = blossom to stem end; 2 = uniform | 2 | 2 |
| Ripening<br>1 = inside out; 2 = uniformity; 3 = outside in | 2 | 2 |
| Stem scar size:<br>1 = small (Roma); 2 = medium (Rutgers); 3 = large | 1 | 1 |
| Core:<br>1 = coreless (absent or smaller than 6 × 6 mm); 2 = present | 1 | 1 |
| Epidermis color:<br>1 = colorless; 2 = yellow | 2 | 2 |
| Epidermis:<br>1 = normal; 2 = easy-peel | 2 | 2 |
| Epidermis texture:<br>1 = tender; 2 = average; 3 = tough | 3 | 3 |
| thickness of pericarp: | 7.7 mm | 6.72 mm |
| Resistance to fruit disorder: | | |
| | not tested | not tested |
| Viral diseases:<br>Disease and pest reaction 0= not tested; 1 = highly resistant; 2 = resistance/few symptoms | | |
| Tomato spotted wilt | 2 | 0 |
| Bacteria disease: | | |
| Bacterial speck (*Pseudomonas tomato*) Race 0 | 2 | 1 |
| Fungal diseases: | | |
| *Fusarium* wilt race 1 (*F. oxysporum f. lycopersici*) | 2 | 1 |
| *Fusarium* wilt race 2 | 2 | 1 |
| *Verticillium* wilt race 1 (*V. dahliae*) | 2 | 1 |
| Insects and Pests: | | |
| Root knot nematode (*Meloidogyne* spp.) | 2 | 1 |

TABLE 1-continued

Comparison between NUN 00213 TOP and HEINZ 8504

| | NUN 00213 TOP | HEINZ 8504 |
|---|---|---|
| Chemistry and composition of full-ripe fruits: | | |
| pH | 4.62 | 4.44 |
| Titratable acidity as % citric | 14.8 | 20.2 |
| Total solids | 15.3 | 13.8 |
| Soluble solids as Brix | 5.0 | 5.20 |
| Phenology: | | |
| Seeding to 50% growth (1 open on 50% of plants) | 34 days | 33 days |
| Seed to once harvest | 125 days | 130 days |
| Fruit season 1 = long (Marglobe); 2 = medium (Westover); 3 = short, concentrated (VF 145); 4 = very concentrated (UC82) | 4 | 3 |
| Relative maturity in areas tested: 1 = early; 2 = medium early; 3 = medium; 4 = medium late; 5 = late; 6 = variable | 3 | 5 |
| Adaptation: | | |
| Culture: 1 = field; 2 = greenhouse | 1 | 1 |
| Principle use(s): 1 = home garden; 2 = fresh market; 3 = whole-pack canning; 4 = concentrated products; 5 = other: Dice | 3 + 4 + 5 | 4 |
| Machine harvest: 1 = not adapted; 2 = adapted | 2 | 2 |
| Regions to which adaptation has been demonstrated: 1 = Northeast; 2 = Mid Atlantic; 3 = Southeast; 4 Florida; 5 = Great Plains, 6 = south central; 7 = Intermountain West; 8 = Northwest; 9 = California (Sacramento and Upper San Joaquin Valley); 10 = California (Coastal Areas); 11 California (Southern San Joaquin Valley & desserts) | 11 + 9 | 9 + 11 |

*These are typical values. Values may vary due to environment. Other values that are substantially equivalent (p ≤ 0.05) are also within the scope of the invention.

In another embodiment the invention relates to a tomato plant, or a part thereof which does not significantly differ from the plant of the invention (i.e. NUN 00209) in any of the characteristics of Table 1, when grown under the same conditions.

REFERENCES

The following references, to the extent that they provide exemplary procedural or other details supplementary to those set forth herein, are specifically incorporated herein by reference:
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
U.S. Pat. No. 6,806,399
WO 99/31248
EP 0 534 858
WO 2014076249
Choi et al., Plant Cell Rep., 13: 344-348, 1994.
Ellul et al., Theor. Appl. Genet., 107:462-469, 2003.
Nature Protocols Vol. 9, Pages: 761-772 (2014) DOI: doi: 10.1038/nprot.2014.049

What is claimed is:

1. A seed of tomato plant of variety NUN 00213 TOP, a representative sample of seed of said variety having been deposited under NCIMB Accession Number 42560.

2. A plant produced by growing the seed of claim 1.

3. A plant part of the plant of claim 2.

4. The plant part of claim 3, further defined as a leaf, pollen, an ovule, a fruit, a scion, a rootstock or a cell.

5. A tomato plant, or a part thereof, which does not differ from the plant of claim 2 in any of the characteristics of Table 1, or a plant or a part thereof having all the physiological and morphological characteristics of the tomato plant of claim 2, when grown under the same conditions.

6. A tissue culture of regenerable cells of the plant of claim 2.

7. A tissue culture of regenerable cells of the plant of claim 2, comprising cells or protoplasts from a plant part of the plant of claim 2 selected from the group consisting of meristems, cotyledons, leaves, anthers, roots, root tips, pistil, flower and stalks.

8. A tomato plant regenerated from the tissue culture of claim 6 having all the physiological and morphological characteristics of a plant of variety NUN 00213 TOP, a representative sample of seed of said variety having been deposited under NCIMB Accession Number 42560.

9. A tomato plant regenerated from the tissue culture of claim 7, retaining all the physiological and morphological characteristics of a plant of variety NUN 00213 TOP as listed in Table 1, when grown under the same conditions, a representative sample of seed of NUN 00213 TOP having been deposited under NCIMB Accession Number 42560.

10. A method of vegetatively propagating the plant of claim 2 comprising the steps of:
    (a) collecting tissue capable of being propagated from the plant according to claim 2;
    (b) cultivating said tissue to obtain proliferated shoots; and
    (c) rooting said proliferated shoots to obtain rooted plantlets.

11. The method of claim 10, further comprising growing plants from said rooted plantlets.

12. A method of crossing tomato plants comprising crossing the plant of claim 2 with a second tomato plant one or more times, selecting progeny from said crossing, and optionally allowing the progeny to form seed.

13. A method of introducing a desired trait into a tomato variety comprising:
    (a) crossing the plant of claim 2 with a second tomato plant that comprises a desired trait to produce F1 progeny;
    (b) selecting an F1 progeny that comprises the desired trait;
    (c) crossing the selected F1 progeny with the plant of claim 2 to produce backcross progeny;
    (d) selecting backcross progeny comprising the desired trait and all or essentially all the physiological and morphological characteristic of the plant of claim 2; and optionally
    (e) repeating steps (c) and (d) three or more times in succession to produce selected fourth or higher backcross progeny that comprises the desired trait.

14. A method of producing a plant comprising an added desired trait, the method comprising introducing a transgene conferring the desired trait into the plant according to claim 2.

15. A method for producing a seed comprising the steps of:
   (a) crossing the tomato plant of claim 2 with a second tomato plant; and
   (b) allowing seed obtained from the cross to form.

16. The method of claim 15 further comprising the steps of:
   (c) crossing a plant grown from the seed of step (b) with itself or another tomato plant to yield additional tomato seed;
   (d) growing said additional tomato seed of step (c) to yield additional tomato plants; and optionally
   (e) repeating the crossing and growing steps of (c) and (d).

17. The method of claim 15, wherein the second tomato plant is of an inbred tomato variety.

18. A plant comprising the scion of claim 4.

19. A plant comprising the rootstock of claim 4.

20. A method of producing a tomato fruit comprising:
   (a) obtaining the plant according to claim 2, wherein the plant has been cultivated to maturity; and
   (b) collecting a tomato fruit from the plant.

\* \* \* \* \*